United States Patent
Obara et al.

(10) Patent No.: US 6,525,192 B2
(45) Date of Patent: *Feb. 25, 2003

(54) LOW-SUBSTITUTED HYDROXYPROPYL CELLULOSE AND PROCESS FOR PRODUCING SAME

(75) Inventors: Sakae Obara, Niigata-ken (JP); Hiroshi Umezawa, Niigata-ken (JP); Naosuke Maruyama, Niigata-ken (JP); Fumie Tanno, Niigata-ken (JP)

(73) Assignee: Shin-Etu Chemical Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 72 days.

(21) Appl. No.: 09/309,532

(22) Filed: May 11, 1999

(65) Prior Publication Data

US 2002/0016452 A1 Feb. 7, 2002

(30) Foreign Application Priority Data

May 12, 1998 (JP) .......................................... 10-128357

(51) Int. Cl.$^7$ ...................... C08B 11/20; C08B 11/193; A61K 31/72
(52) U.S. Cl. .............................. 536/85; 536/84; 536/88; 536/89; 536/91
(58) Field of Search ............................. 536/30, 56, 88, 536/91, 84, 85

(56) References Cited

U.S. PATENT DOCUMENTS

| | | | |
|---|---|---|---|
| 2,488,631 A | 11/1949 | Kunz | 260/231 |
| 3,251,824 A | 5/1966 | Battista | 260/230 |
| 3,290,218 A | 12/1966 | de Jong | 167/82 |
| 3,852,421 A | 12/1974 | Koyanagi et al. | 424/94 |
| 4,091,205 A | 5/1978 | Onda et al. | 536/85 |
| 4,159,345 A * | 6/1979 | Takeo et al. | 424/362 |
| 4,329,451 A | 5/1982 | Zweigle | 536/77 |
| 4,415,124 A | 11/1983 | Carduck et al. | 241/28 |
| 4,454,108 A | 6/1984 | Iida et al. | 424/16 |
| 4,716,186 A | 12/1987 | Portnoy et al. | 524/50 |
| 5,200,194 A | 4/1993 | Edgren et al. | 424/473 |
| 5,516,531 A | 5/1996 | Makino et al. | 424/492 |

FOREIGN PATENT DOCUMENTS

| | | | | |
|---|---|---|---|---|
| EP | 0997148 A1 | 5/2000 | ......... | A61K/31/785 |
| GB | 2 262 527 A | 6/1993 | ........... | C08B/11/20 |
| JP | 48103717 A | 12/1973 | ............ | A61K/9/20 |
| JP | 07324101 A | 12/1995 | ........... | C08B/11/08 |
| JP | 10265501 | 10/1998 | ........... | C08B/11/08 |
| JP | 10279601 A | 10/1998 | ........... | C08B/11/08 |
| WO | WO97/03654 | 2/1997 | ............ | A61K/9/14 |

OTHER PUBLICATIONS

European Office Action, Date: Oct. 11, 2000, European Patent Application No. 99108634.9–2115–.

European Search Report, Date: Mar. 9, 2000, European Patent Application No. 99108634.9–2115–.

* cited by examiner

Primary Examiner—James O. Wilson
Assistant Examiner—Howard Owens
(74) Attorney, Agent, or Firm—Myers Bigel Sibley & Sajovec

(57) ABSTRACT

The present invention provides a low-substituted hydroxypropyl cellulose having a loose bulk density of not less than 0.40 g/mL and a tap bulk density of not less than 0.60 g/mL and a process for producing the same.

6 Claims, No Drawings

LOW-SUBSTITUTED HYDROXYPROPYL CELLULOSE AND PROCESS FOR PRODUCING SAME

BACKGROUND OF THE INVENTION

This invention relates to a low-substituted hydroxypropyl cellulose which is added to solid pharmaceutical preparations and the like as a binder, disintegrant or excipient, and a process for producing the same.

Low-substituted hydroxypropyl cellulose (hereinafter referred to as L-HPC), which is a pharmaceutical additive described in the Japanese Pharmacopoeia, comprises a cellulosic polymer which is added to solid pharmaceutical preparations such as tablets and granules. L-HPC functions as a binder and a disintegrant, and may be used as an excipient owing to its little interaction with active ingredients. L-HPC is a low-substituted hydroxypropyl ether of cellulose, and its hydroxypropoxyl content is in the range of 5.0 to 16.0%. In this respect, L-HPC is different in properties from pharmacopoeial hydroxypropyl cellulose (HPC) having a hydroxypropoxyl content of 53.4 to 77.5%. It is described in Japanese Patent Publication Nos. 42792/'71 and 53100/'82 that L-HPC is being used as an additive for pharmaceutical preparations.

The methods for forming tablets include a direct compression method in which a mixture composed of active ingredients and additives is directly formed into tablets, and a wet granulation method in which a mixture composed of active ingredients and additives is granulated by kneading it with a suitable solvent such as a binder solution or water, and the resulting granules are dried and formed into tablets. Where a powder composed of active ingredients and additives has poor flowability, the latter method is employed to enhance its flowability.

The typical granulation processes employed in the wet granulation method include agitation granulation using a high-speed agitator, and fluidized bed granulation using a fluidized bed.

In recent years, fluidized bed granulation has come to be frequently employed because it yields a granulated material having a narrower particle size distribution and permits easier process control, as compared with agitation granulation. However, if fluidized bed granulation is applied to L-HPC, the resulting granulated material will be very bulky and have poor flowability. Since this granulated material fails to flow out smoothly from the hopper of a compression machine, it may be impossible to form tablets, or the resulting tablets may show considerable variation in weight. Thus, it has been very difficult to use L-HPC in fluidized bed granulation.

An object of the present invention is to provide an L-HPC which can also accommodate fluidized bed granulation.

In this connection, Japanese Patent Provisional Publication No. 279601/'98 discloses an L-HPC having specifically defined viscosity, tap apparent density, angle of repose, average particle diameter and other properties. Moreover, Japanese Patent Provisional Publication No. 324101/'95 discloses an L-HPC characterized by an angle of repose of not greater than 45 degrees and a degree of swelling of not less than 100%. When fluidized bed granulation is applied to these L-HPCs, a slight improvement over conventional products is achieved, but the results thus obtained are still less than satisfactory.

SUMMARY OF THE INVENTION

There are provided in accordance with the present invention a low-substituted hydroxypropyl cellulose which permits the preparation of a suitable compression material by using fluidized bed granulation, and a process for producing the same.

The present inventor has succeeded in developing an L-HPC which is highly suitable for practical use in fluidized bed granulation, by improving its powder properties from another point of view. That is, one aspect of the present invention is an L-HPC having a loose bulk density of not less than 0.40 g/mL and a tap bulk density of not less than 0.60 g/mL.

Another aspect of the present invention is a process for producing the inventive L-HPC which comprises the steps of dipping pulp in an alkaline solution to prepare alkali cellulose, reacting the alkali cellulose with propylene oxide, dissolving the resulting product partially in water or an alkaline solvent, precipitating the product by neutralization with an acid, and washing, drying and grinding the precipitated product, wherein the product is completely dissolved prior to the neutralization with an acid.

DETAILED DESCRIPTION OF THE PREFERRED EMBODIMENTS

The term "loose bulk density" as used herein refers to a bulk density in a loosely packed state. This can be measured by providing a cylindrical vessel having a diameter of 5.03 cm and a height of 5.03 cm (and hence a capacity of 100 mL), introducing a sample uniformly into the vessel from above while passing it through a 24 mesh screen, leveling the top surface of the sample, and then weighing it.

The term "tap bulk density" refers to a bulk density measured after a sample is closely packed by tapping. Tapping is an operation for bringing a sample into a closely packed state by letting a vessel filled with the sample fall repeatedly from a certain height and thus giving mild shocks to the bottom of the vessel. Actually, after the top surface of the sample is leveled and weighed to measure its loose bulk density, a cap is attached to the top of the vessel. Then, the powder is added thereto until it reaches the upper end of the cap, and then tapped 180 times from a tapping height of 1.8 cm. After completion of the tapping, the cap was removed, the top surface of the powder was leveled at the upper end of the vessel, and the powder was weighed. The bulk density measured in this state is regarded as the tap bulk density. The above-described measuring procedure can be carried out by using a powder tester manufactured by Hosokawa Micron Corp.

The present inventor has found that an L-HPC whose loose bulk density and tap bulk density are not less than certain values can be used in fluidized bed granulation. When this L-HPC is used in fluidized bed granulation, the resulting granulated material is heavy and highly flowable, and can hence be practically used for compression purposes.

The object of the present invention is accomplished when the L-HPC has a loose bulk density of not less than 0.40 g/mL and a tap bulk density of not less than 0.60 g/mL. However, it is preferable that the ratio of the loose bulk density to the tap bulk density be not greater than a certain level. The level is defined by a degree of compaction of not greater than 35%. The degree of compaction is a degree of volume reduction and can be determined according to the following equation.

Degree of compaction (%)=[{(tap bulk density) −(loose bulk density)}/(tap bulk density)]×100

The degree of compaction may be regarded as a parameter representing the flowability of a power. Other parameters representing flowability include characteristic values such as angle of repose and angle of spatula, and a flowability index is known as a parameter defined by putting all of them together. The flowability index is a parameter which was proposed by Carr in order to evaluate flowability [R. L. Carr, Chem. Eng., 72, January 18, 163and February 1,69 (1965);6, October 13,7(1969)], and a detailed description thereof is given in "An Illustrated Explanation of Powder Properties (revised and enlarged edition)" (edited by the Japanese Society of Powder Technology and the Japanese Association of Powder Engineers, Nikkei Technical Books, 1985), page 151. The flowability index of a powder can be determined by measuring four characteristic values (i.e., angle of repose, degree of compaction, angle of spatula, and degree of aggregation) by means of a powder tester, determining the respective indices from the measured values, and summing them up. The L-HPC of the present invention preferably has a flowability index of not less than 60.

The L-HPC of the present invention preferably has an angel of repose of not greater than 40 degrees. The angle of repose can be determined by pouring a powder onto a disc having a diameter of 8 cm through a funnel and measuring the vertical angle of the resulting conical mass of powder with a protractor.

It has been found that the L-HPC of the present invention can be produced according to the process described below.

That is, pulp is soaked in an alkaline solution to yield alkali cellulose, and this is reacted with propylene oxide. Up to this stage, the process of the present invention is the same as the conventional one. The present inventor has found that, in the succeeding step where the product is added to and dissolved in water or water made alkaline, the state of the product affects the flowability of the L-HPC. Specifically, in the conventional process where the product is partially neutralized to bring it into a partially dissolved state, the bulk density of the L-HPC is regulated by controlling the degree of dissolution and thus altering the fiber content. However, the present inventor has found that, among others, the flowability of the L-HPC is enhanced when the product is brought into a completely dissolved state in this step.

The term "completely dissolved state" as used herein means a state in which the product has lost its form almost completely. That is, this comprehends not only a perfectly clear slurry, but also an opaque slurry or a state in which, for example, 5 to 10 small lumps of the product remain in 3 L of a slurry. The dissolved product is in the form of a highly viscous slurry and requires the use of a mixing machine having strong agitation power, such as a kneader. Thereafter, the L-HPC is precipitated by neutralizing the slurry with an acid (e.g., hydrochloric acid) as usual. The precipitated L-HPC is recovered, washed, dried and ground to yield a final product.

Moreover, the present inventor has also found that the conditions for the preparation of alkali cellulose affects the degree of dissolution of the product. More specifically, the product can readily be brought into a completely dissolved state when the alkaline solution used for dipping purposes comprises a sodium hydroxide solution having concentration of not greater than 45% by weight.

Conventionally, a 49% solution of sodium hydroxide has been used. In the present invention, however, it is believed that the uniformity of the reaction and the solubility of the product are increased by reducing its concentration.

EXAMPLES

The present invention is further illustrated by the following examples. It is to be understood that the present invention is not limited to these examples.

Example 1

Wood pulp was soaked in a 40 wt. % aqueous solution of sodium hydroxide and then pressed to yield alkali cellulose. A reactor was charged with 800 g of this alkali cellulose, and then purged with nitrogen. After purging, 85.6 g of propylene oxide was added to the reactor, and reaction was effect, with stirring, at 40° C. for 1 hour and at 70° C. for 1 hour to yield a product.

A 5 L double-arm kneader was charged with 2 L of hot water at 65° C. The above product was added thereto, kneaded for about 10 minutes until the form of the product disappeared almost completely (i.e., to such an extent that 5 to 10 small lumps of the product remained in about 3 L of the slurry), and then precipitated by neutralization with acetic acid. After this product was washed with hot water at 90° C., dewatered by pressing, and dried, the resulting solid was ground with a high-speed rotating impact grinder to yield L-HPC having a hydroxypropoxyl content of 11%.

Example 2

L-HPC was prepared under the same conditions as in Example 1, except that, in the dissolution step, the product was kneaded for about 30 minutes until no small lumps of the product were observed.

Comparative Example 1

Alkali cellulose was prepared and reacted in the same manner as in Example 1. However, in the dissolution step, a portion of the acetic acid for neutralization was added to hot water at 65° C. prior to the addition of the product. Thus, the product was brought into a partially dissolved state and neutralized with the remaining acetic acid. Thereafter, the same procedure as in Example 1 was followed to yield a powder of L-HPC.

Comparative Example 2

L-HPC was prepared by dipping pulp in a 49 wt. % aqueous solution of sodium hydroxide and thereafter following the same procedure as in Example 1. In the dissolution step, the product was kneaded for 40 minutes, but its dissolved state was less satisfactory than that in Example 1. However, its dissolution was more advanced than the partially dissolved state in Comparative Example 1. Thereafter, the same procedure was followed to yield a powder of L-HPC.

Comparison of Powder Properties

With regard to the L-HPCs prepared in Examples 1 and 2 and Comparative Examples 1 and 2, and a commercially available L-HPC (Comparative Example 3), some powder properties of a sample of each L-HPC were measured with a powder tester manufactured by Hosokawa Micron Corp. The results thus obtained are shown in Table 1.

TABLE 1

| Sample | Loose bulk density (g/mL) | Tap bulk density (g/mL) | Degree of compaction (%) | Flowability index | Angle of repose (degrees) |
|---|---|---|---|---|---|
| Example 1 | 0.430 | 0.652 | 34.1 | 62 | 40 |
| Example 2 | 0.503 | 0.697 | 27.8 | 69 | 37 |
| Comparative Example 1 | 0.335 | 0.597 | 43.9 | 49 | 52 |

TABLE 1-continued

| Sample | Loose bulk density (g/mL) | Tap bulk density (g/mL) | Degree of compaction (%) | Flowability index | Angle of repose (degrees) |
|---|---|---|---|---|---|
| Comparative Example 2 | 0.392 | 0.612 | 35.9 | 58 | 42 |
| Comparative Example 3 (note) | 0.279 | 0.502 | 44.4 | 46 | 52 |

(Note)
Commercially available L-HPC (manufactured by Shin-Etsu Chemical Co., Ltd.)

Fluidized Bed Granulation Tests

A mixture composed of 160 g of acetaminophen, 100 g of a sample of the L-HPC obtained in each of the Examples and Comparative Examples, 98 g of lactose, and 42 g of corn starch was charged into a small-sized fluidized bed (Multiplex MP-01; manufactured by Powrex Corp.), and fluidized at an inlet air temperature of 70° C. Then, granulation was carried out by spraying a binder comprising a 5% aqueous solution of HPC-L (manufactured by Nippon Soda Co., Ltd.). The bulk density and angle of repose of the resulting granulated material were measured. Moreover, the granulated material was introduced into the hopper of a small-sized compression machine, and its state of outflow was observed. The results this obtained are shown in Table 2.

TABLE 2

| | Properties of granlated material | | |
|---|---|---|---|
| Sample | Bulk density (g/mL) | Angle of repose (degrees) | Outflow from hopper of compression machine |
| Example 1 | 0.42 | 38 | Good |
| Example 2 | 0.43 | 38 | Good |
| Comparative Example 1 | 0.23 | 51 | Did not flow out easily because of bridging |
| Comparative Example 2 | 0.38 | 43 | Generally flowed out well, but sometimes suffered from bridging |
| Comparative Example 3 | 0.22 | 52 | Did not flow out easily because of bridging |

As a result of fluidized bed granulation, the L-HPCs of Examples 1 and 2 gave granulated materials which were heavier and more easily flowable than those prepared from the L-HPCs of Comparative Examples 1–3.

Many other variations and modifications of the invention will be apparent to those skilled in the art without departing from the spirit and scope of the invention. The above-described embodiments are, therefore, intended to be merely exemplary, and all such variations and modifications are intended to be included within the scope of the invention as defined in the appended claims.

The disclosure of Japanese Patent Application No. 10-128357 filed on May 12, 1998 including specification, claims, drawings and summary are incorporated herein by reference in its entirety.

What is claimed is:

1. A low-substituted hydroxypropyl cellulose having a loose bulk density of not less than 0.40 g/mL, a tap bulk density of not less than 0.60 g/mL, a hydroxypropyl content of from 5.0 percent to 16.0 percent, and a degree of compaction not greater than 35 percent, and wherein the low-substituted hydroxypropyl cellulose has a flowability index of not less than 60.

2. A low-substituted hydroxypropyl cellulose having a loose bulk density of not less than 0.40 g/mL, a tap bulk density of not less than 0.60 g/mL, a hydroxypropyl content of from 5.0 percent to 16.0 percent, and a degree of compaction not greater than 35 percent, and wherein the low-substituted hydroxypropyl cellulose has an angle of repose of not greater than 40 degrees.

3. A low-substituted hydroxypropyl cellulose having a loose bulk density of not less than 0.40 g/mL, a tap bulk density of not less than 0.60 g/mL, a hydroxypropyl content of from 5.0 percent to 16.0 percent, and a degree of compaction not greater than 35 percent, and wherein the low-substituted hydroxypropyl cellulose has a flowability index of not less than 60 and an angle of repose of not greater than 40 degrees.

4. A method of forming a tablet comprising the low-substituted hydroxypropyl cellulose according to claim 1.

5. A method of forming a tablet comprising the low-substituted hydroxypropyl cellulose according to claim 2.

6. A method of forming a tablet comprising the low-substituted hydroxypropyl cellulose according to claim 3.

* * * * *